US009049993B2

(12) United States Patent
Tanishima et al.

(10) Patent No.: US 9,049,993 B2
(45) Date of Patent: Jun. 9, 2015

(54) APPARATUS FOR BIOLOGICAL SIGNAL MEASUREMENT AT POINT OF END-TIDAL

(75) Inventors: Masami Tanishima, Tokyo (JP); Mitsushi Hyogo, Tokyo (JP); Takashi Mato, Saitama (JP)

(73) Assignee: NIHON KOHDEN CORPORATION, Tokyo (JP)

( * ) Notice: Subject to any disclaimer, the term of this patent is extended or adjusted under 35 U.S.C. 154(b) by 616 days.

(21) Appl. No.: 12/714,774

(22) Filed: Mar. 1, 2010

(65) Prior Publication Data

US 2010/0222650 A1 Sep. 2, 2010

(30) Foreign Application Priority Data

Mar. 2, 2009 (JP) .................................. 2009-048321

(51) Int. Cl.
| | |
|---|---|
| *A61B 5/00* | (2006.01) |
| *A61B 5/0205* | (2006.01) |
| *A61B 5/03* | (2006.01) |
| *A61B 5/083* | (2006.01) |
| *G06F 19/00* | (2011.01) |

(52) U.S. Cl.
CPC ............. *A61B 5/0205* (2013.01); *A61B 5/7271* (2013.01); *A61B 5/03* (2013.01); *A61B 2505/03* (2013.01); *G06F 19/3487* (2013.01); *A61B 5/74* (2013.01); *A61B 5/7282* (2013.01); *A61B 2505/05* (2013.01); *G06F 19/34* (2013.01); *A61B 5/0836* (2013.01); *A61B 2505/01* (2013.01); *A61B 5/7239* (2013.01)

(58) Field of Classification Search
CPC ............ A61B 5/03–5/031; A61B 5/08; A61B 5/087–5/0878; A61B 5/72; A61B 5/7282; A61B 5/74; A61B 5/0205; G06F 19/34; G06F 19/3487

USPC ................. 600/300–301, 363–365, 373–374, 600/377–379, 382–384, 386–394, 481, 485, 600/500–503, 509, 515–519, 529–531, 600/544–547, 549, 587–595; 128/920–925
See application file for complete search history.

(56) References Cited

U.S. PATENT DOCUMENTS 5,069,222 A * 12/1991 McDonald, Jr. ............... 600/537
5,694,924 A 12/1997 Cewers
(Continued)

FOREIGN PATENT DOCUMENTS

| EP | 1 769 737 A1 | 4/2007 |
|---|---|---|
| JP | 09-122241 A | 5/1997 |

(Continued)

OTHER PUBLICATIONS

You, B. et al in "Expiratory capnography in asthma", Eur Respir J, 1994, 7, 318-323.*
Kim, S. et al in "Intracranial Pressure Variation Associated with Changes in End-Tidal CO2", Proceedings of the 28th IEEE EMBS Annual International Conference New York City, USA, Aug. 30-Sep. 3, 2006, p. 9-12.*

(Continued)

*Primary Examiner* — William Thomson
*Assistant Examiner* — Marie Archer
(74) *Attorney, Agent, or Firm* — Sughrue Mion, PLLC (57) ABSTRACT

A biological signal measuring apparatus includes: a pressure sensor which measures a pressure in a living body; a respiratory sensor which measures respiratory information; and an outputting unit which detects an end-tidal based on the respiratory information measured by the respiratory sensor and which outputs a pressure value based on the pressure measured by the pressure sensor when detecting the end-tidal.

19 Claims, 5 Drawing Sheets

(56) References Cited

U.S. PATENT DOCUMENTS

| | | | |
|---|---|---|---|
| 6,015,388 A * | 1/2000 | Sackner et al. | 600/529 |
| 6,188,407 B1 * | 2/2001 | Smith et al. | 715/841 |
| 6,402,697 B1 * | 6/2002 | Calkins et al. | 600/532 |
| 6,796,305 B1 * | 9/2004 | Banner et al. | 128/204.21 |
| 2002/0120207 A1 * | 8/2002 | Hoffman | 600/538 |
| 2003/0100845 A1 | 5/2003 | Eide | |
| 2003/0214409 A1 * | 11/2003 | Hickle | 340/573.1 |
| 2005/0177096 A1 * | 8/2005 | Bollish et al. | 604/65 |
| 2006/0287604 A1 | 12/2006 | Hickey | |
| 2007/0073170 A1 * | 3/2007 | Danehorn et al. | 600/484 |
| 2007/0088221 A1 | 4/2007 | Stahmann | |
| 2007/0089744 A1 | 4/2007 | Wiese | |
| 2007/0129647 A1 * | 6/2007 | Lynn | 600/538 |
| 2007/0156193 A1 | 7/2007 | Cho et al. | |
| 2008/0188733 A1 * | 8/2008 | Al-Ali et al. | 600/364 |
| 2008/0230060 A1 * | 9/2008 | Tham | 128/204.21 |
| 2008/0281168 A1 * | 11/2008 | Gibson et al. | 600/301 |
| 2008/0300471 A1 * | 12/2008 | Al-Ali et al. | 600/301 |
| 2009/0131805 A1 * | 5/2009 | O'Brien et al. | 600/485 |
| 2012/0095304 A1 * | 4/2012 | Biondi | 600/301 |

FOREIGN PATENT DOCUMENTS

| | | |
|---|---|---|
| JP | 2000-033079 A | 2/2000 |
| JP | 2004-016802 A | 1/2004 |
| JP | 2004-528104 A | 9/2004 |
| WO | 2007-047287 A2 | 4/2007 |
| WO | 2008/118951 A1 | 10/2008 |

OTHER PUBLICATIONS

Garrad J. et al "The Effect of Respiratory Therapy on Intracranial Pressure in Ventilated Neurosurgical Patients"; The Australian Journal of Physiotherapy. vol. 32, No. 2, 1986, p. 107-111.*

Bouma, J. G. et al "Blood pressure and intracranial pressure-volume dynamics in severe head injury: relationship with cerebral blood flow"; J. Neurosurg 77:15-19, 1992.*

Clarke, J.P. "The effects of inverse ratio ventilation on intracranial pressure: a preliminary report"; Intensive Care Med (1997) 23:106-109.*

Office Action, dated Dec. 17, 2012, issued by the Japanese Patent Office in counterpart Japanese Application No. 2009-048321.

Morioka, Nobutada et al., "Evaluation of a compact device for Capnometry of Mainstream Type Compared with One of Side-stream Type in a Postoperative Care Unit", Japanese Journal of Anesthesiology (Masui), Dec. 2006, Kokuseido Co., Ltd., vol. 55, No. 12, pp. 1496-1501.

Office Action issued by the Japanese Patent Office dated May 31, 2013 in corresponding Application No. 2009-048321.

Office Action, dated Oct. 18, 2013, issued by the Japanese Patent Office, in counterpart Application No. 2009-048321.

Extended European Search Report, dated Aug. 1, 2012, issued by the European Patent Office in counterpart European Application No. 10155047.3.

* cited by examiner

APPARATUS FOR BIOLOGICAL SIGNAL MEASUREMENT AT POINT OF END-TIDAL

BACKGROUND OF THE INVENTION

The present invention relates to a biological signal measuring apparatus which can stably measure a correct biological signal such as the invasive blood pressure or the intracranial pressure while suppressing respiratory variation included in the biological signal.

In patient monitoring, the blood pressure is regarded as an important index. For a severe patient, particularly, it is usual to invasively monitor the arterial and venous pressures. In the invasive blood pressure measurement, a catheter or the like is placed in a vessel or the heart, and a blood pressure waveform or a blood pressure value is continuously measured.

The heart exists in the chest cavity, and hence an invasive blood pressure waveform is affected by variation of the intrapleural pressure due to the respiration of the patient, thereby causing a problem in that a correct blood pressure value is not obtained. Particularly, the central venous pressure (CVP) in the vicinity of the right atrial is low, and hence markedly affected by variation of the intrapleural pressure.

In order to suppress such variation of an invasive blood pressure waveform, therefore, an averaging process is performed on obtained values of the invasive blood pressure in a related art.

In the related-art technique for suppressing an invasive blood pressure waveform by the averaging process, in the case where the respiratory variation is large, a sufficient effect cannot be obtained. In a low-pressure system (for example, the central venous pressure or the pulmonary arterial pressure) which is largely affected by variation of the intrapleural pressure, the respiratory variation component is relatively large with respect to the blood pressure value, and hence a stable blood pressure measurement is hardly performed. As described above, although a blood pressure of the low-pressure system reflects the conditions of the heart function and the circulatory blood volume which are clinically very useful, the blood pressure is largely affected by respiratory variation. A technique for eliminating or suppressing the influence has not yet been established.

For example, also a related-art technique is known in which a calculation process of eliminating an influence due to a respiratory component causing an artifact from a measured blood pressure waveform is performed to suppress variation of an invasive blood pressure waveform (see EP1769737A1).

According to the related-art technique, data can be continuously measured, but the measured data are affected depending on the method of performing a calculating process, thereby causing a possibility that a correct measurement is hindered. There is another problem in that the calculating process is complicated. When noises are superimposed only on a respiratory signal, moreover, there arises a further problem in that the blood pressure waveform is affected.

SUMMARY

It is therefore an object of the invention to provide a biological signal measuring apparatus which can stably measure a correct biological signal such as an invasive blood pressure or an intracranial pressure while suppressing respiratory variation included in the biological signal, without causing the configuration and the process to be complicated.

In order to achieve the object, according to the invention, there is provided a biological signal measuring apparatus comprising:

a pressure sensor which measures a pressure in a living body;

a respiratory sensor which measures respiratory information; and an outputting unit which detects an end-tidal based on the respiratory information measured by the respiratory sensor and which outputs a pressure value based on the pressure measured by the pressure sensor when detecting the end-tidal.

The pressure measured by the pressure sensor may include an invasive blood pressure, and the pressure value output by the outputting unit may include an invasive blood pressure value.

The pressure measured by the pressure sensor may include an intracranial pressure, and the pressure value measured by the outputting unit may include an intracranial pressure value.

The invasive blood pressure may be at least one of a central venous pressure, a pulmonary arterial pressure, a pulmonary arterial wedge pressure, an arterial-pressure, and an intracardiac pressure.

The respiratory sensor may be one of an airway pressure sensor, a respiratory flow sensor, a carbon dioxide sensor, a respiratory volume sensor, a respiratory thermal sensor, and an impedance respiratory sensor.

The respiratory sensor may be of a mainstream type.

The end-tidal may be detected from a falling edge of a differentiated waveform of a capnograph.

The end-tidal may be detected by obtaining a timing when expiration is switched to inspiration in an airway pressure, a respiratory flow, or a respiratory volume waveform.

The pressure value output by the outputting unit may correspond to one of an average pressure obtained by a moving average and an average pressure of one heartbeat period.

Both of a value of the pressure measured by the pressure sensor and the pressure value output by the outputting unit may be simultaneously displayed, or one of the value of the pressure measured by the pressure sensor and the pressure value output by the outputting unit may be selectively displayed.

The biological signal measuring apparatus may further include: a selecting unit. The respiratory sensor may be configured by a plurality of respiratory sensors including an airway pressure sensor, a respiratory flow sensor, a carbon dioxide sensor, a respiratory volume sensor, a respiratory thermal sensor, and an impedance respiratory sensor, and the selecting unit may select at least one of respiratory information which are measured by the plurality of respiratory sensors.

DETAILED DESCRIPTION OF EMBODIMENTS

Figure 1:
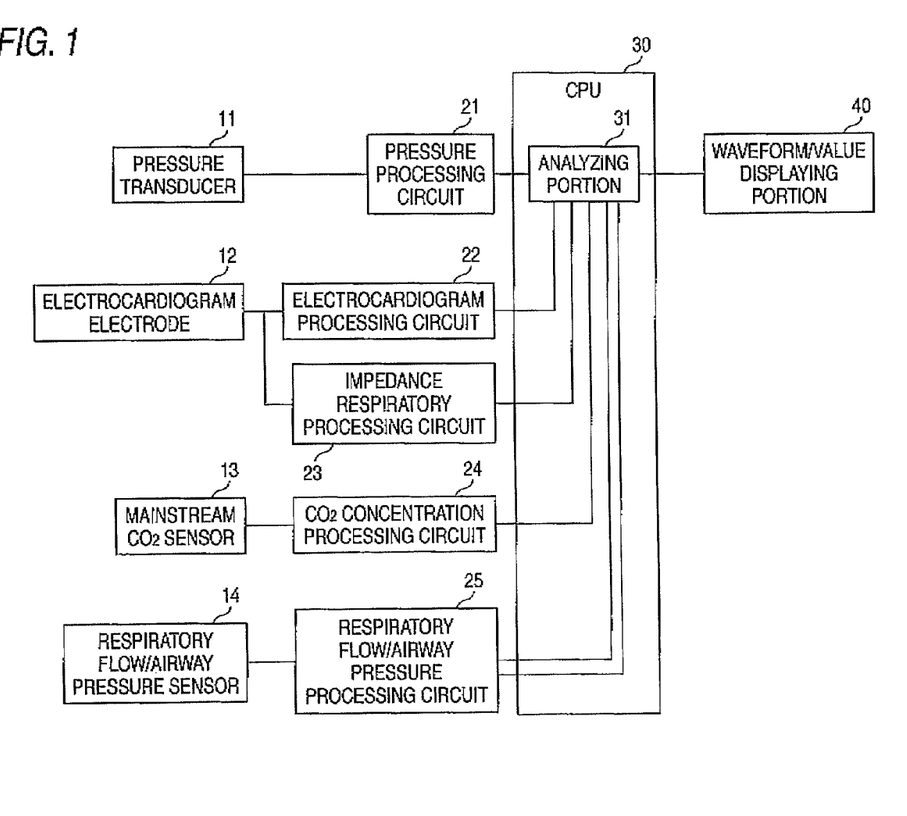
FIG. 1 is a block diagram showing the configuration of an embodiment of the biological signal measuring apparatus of the invention.

Hereinafter, an embodiment of the biological signal measuring apparatus of the invention will be described with reference to the accompanying drawings. FIG. 1 shows the configuration of the biological signal measuring apparatus of the embodiment. The biological signal measuring apparatus includes a pressure transducer 11, electrocardiogram electrodes 12, a mainstream $CO_2$ sensor 13, and a respiratory flow/airway pressure sensor 14.

The pressure transducer 11 is configured by one or more blood pressure sensors which measure the invasive blood pressure and/or one or more intracranial pressure sensor which measures the intracranial blood pressure, and placed at a predetermined position (s) of the living body. In the case where the pressure transducer 11 is a blood pressure sensor which measures the invasive blood pressure, a sensor is disposed which obtains, as the invasive blood pressure, at least one of the central venous pressure (CVP), the pulmonary arterial pressure (PAP), the pulmonary arterial wedge pressure (PCWP), the arterial pressure (ART), and the intracardiac pressure (RAP, RVP, LAP, LVP).

The apparatus is configured so that a pressure processing circuit 21 is connected to the pressure transducer 11 which is a pressure sensor for detecting a pressure, and the output signal of the pressure processing circuit 21 is supplied to a CPU 30. An electrocardiogram processing circuit 22 and an impedance respiratory processing circuit 23 are connected to the electrocardiogram electrodes 12 which constitute a sensor for measuring the rate of the heartbeat. The output signals of the electrocardiogram processing circuit 22 and the impedance respiratory processing circuit 23 are supplied to the CPU 30. As the sensor for measuring the rate of the heartbeat, a plethysmogram sensor, an arterial pressure sensor, or the like may be used in place of the electrocardiogram sensor. The output of the electrocardiogram processing circuit 22 may be used for obtaining the average pressure of one heartbeat period, and, in the case where the average pressure is obtained by the moving average, is not an essential configuration for obtaining the average pressure. The biological signal measuring apparatus of the embodiment is configured so that, in addition to the above, desired sensors for obtaining, for example, the blood oxygen saturation ($SpO_2$) are disposed, and obtained signals are processed and then sent to the CPU 30.

A $CO_2$ concentration processing circuit 24 is connected to the mainstream $CO_2$ sensor 13 which is a sensor for measuring respiratory information, and the output signal of the $CO_2$ concentration processing circuit 24 is supplied to the CPU 30. The respiratory information includes information which can specify the timing (end-tidal) when the expiration and the inspiration are switched over. Specific examples of the respiratory information are the airway pressure, the respiratory flow, the $CO_2$ concentration, the respiratory volume, the respiratory temperature, the impedance respiration, and the like. A respiratory flow/airway pressure processing circuit 25 is connected to the respiratory flow/airway pressure sensor 14 which measures the respiratory information, and the output signals of the respiratory flow/airway pressure processing circuit 25 are supplied to the CPU 30. As a sensor for measuring the respiratory information, a respiratory thermal sensor and a respiratory volume sensor may be employed.

The CPU 30 includes an analyzing portion 31. A pressure waveform signal which is produced by the pressure processing circuit 21, an electrocardiographic waveform signal which is produced by the electrocardiogram processing circuit 22, an impedance respiratory waveform signal which is produced by the impedance respiratory processing circuit 23, a capnograph signal which is produced by the $CO_2$ concentration processing circuit 24, and a respiratory flow signal (the flow in FIG. 2) and airway pressure Paw signal which are produced by the respiratory flow/airway pressure processing circuit 25 are fetched into the analyzing portion 31.

The analyzing portion 31 obtains biological information by using the above-mentioned signals, and sends the information as a biological information waveform and a biological information value to a waveform/value displaying portion 40 configured by a displaying device such as an LCD, and a display controller, thereby displaying a waveform and value of the biological information.

Figure 2:
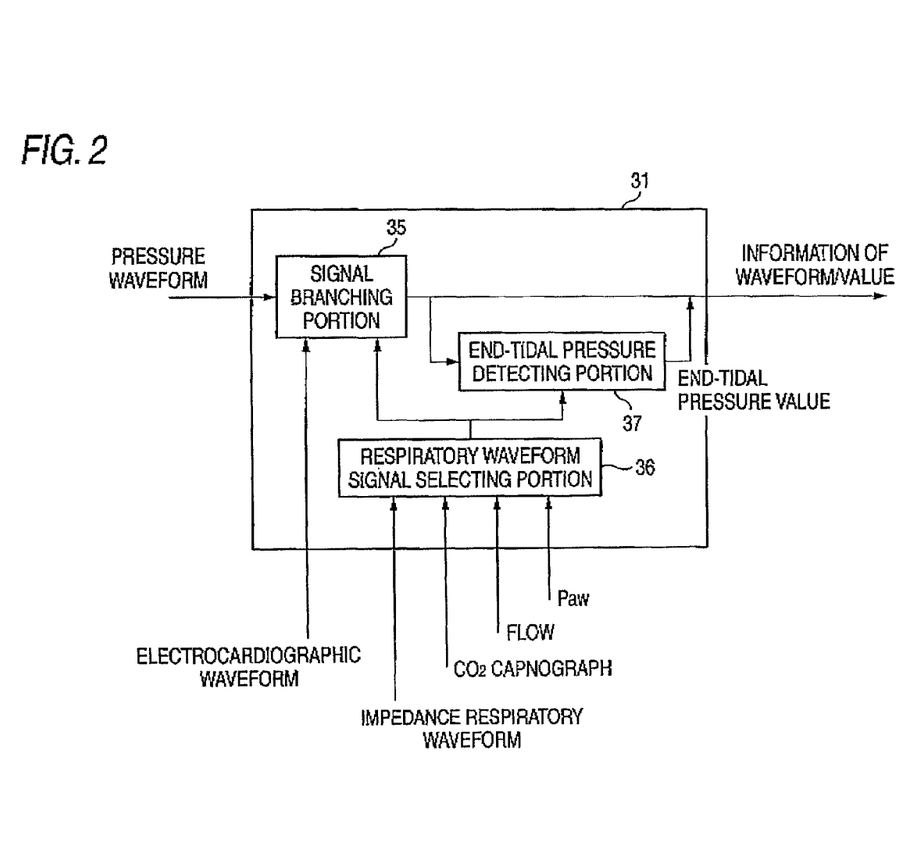
FIG. 2 is a block diagram showing the configuration of a part of the embodiment of the biological signal measuring apparatus of the invention.

As shown in FIG. 2, the analyzing portion 31 includes a signal branching portion 35, a respiratory waveform signal selecting portion 36, and an end-tidal pressure detecting portion 37. The impedance respiratory waveform signal which is produced by the impedance respiratory processing circuit 23, the capnograph signal which is produced by the $CO_2$ concentration processing circuit 24, and the respiratory flow signal and airway pressure Paw signal which are produced by the respiratory flow/airway pressure processing circuit 25 are supplied to the respiratory waveform signal selecting portion 36. The respiratory waveform signal selecting portion 36 supplies these signals to the signal branching portion 35, selects a desired one of the signals, and gives the selected signal to the end-tidal pressure detecting portion 37. The signal selection is performed in the following manner. An inputting device through which an external input is performed on the CPU 30 is disposed, and, as required, one or a desired plurality of the signals are selected and set.

Alternatively, the respiratory waveform signal selecting portion 36 may select a respiratory waveform signal in accordance with an operation of the user. The respiratory waveform signals may be previously provided with priorities. In the case where a problems occurs in a respiratory waveform signal having a high priority (for example, in the case where a sensor is disconnected), a respiratory waveform signal having a next high priority may be selected.

The pressure waveform signal which is produced by the pressure processing circuit 21, and the electrocardiographic waveform signal which is produced by the electrocardiogram processing circuit 22 are supplied to the signal branching portion 35, and also the respiratory waveform signals which are input into the respiratory waveform signal selecting portion 36 are supplied to the signal branching portion. The signal branching portion 35 outputs the pressure waveform signal which is produced by the pressure processing circuit 21, to the end-tidal pressure detecting portion 37 and the waveform/value displaying portion 40.

The end-tidal pressure detecting portion 37 receives the signal which is selected by the respiratory waveform signal selecting portion 36, and respiratory function waveform information which is output from the signal branching portion 35. The end-tidal pressure detecting portion 37 functions as an outputting unit for outputting the pressure value based on the pressure which is obtained by the pressure transducer 11 that serves as a pressure sensor, when the end-tidal is recognized (detected) on the basis of the respiratory information which is obtained by the electrocardiogram electrodes 12, mainstream $CO_2$ sensor 13, and respiratory flow/airway pressure sensor 14 that serve as a respiratory sensor. The end-tidal is a timing at which the expiration is ended, and which is immediately before the beginning of the inspiration. The output value from the end-tidal pressure detecting portion 37 is displayed on the waveform/value displaying portion 40.

The thus configured biological signal measuring apparatus measures a respiratory function signal by using, for example, the central venous pressure (CVP). In this case, the pressure transducer 11 is set so that the central venous pressure of the subject can be obtained, the electrocardiogram electrodes 12, the mainstream $CO_2$ sensor 13, and the respiratory flow/airway pressure sensor 14 are attached to required portions of the subject, respectively, and then the measurement is started.

A blood pressure signal detected by the pressure transducer 11 reaches the pressure processing circuit 21. The pressure processing circuit 21 calculates the blood pressure value (central venous pressure) on the basis of the blood pressure signal, digitizes the value, and outputs the digitized value as the pressure waveform signal.

Figure 3:
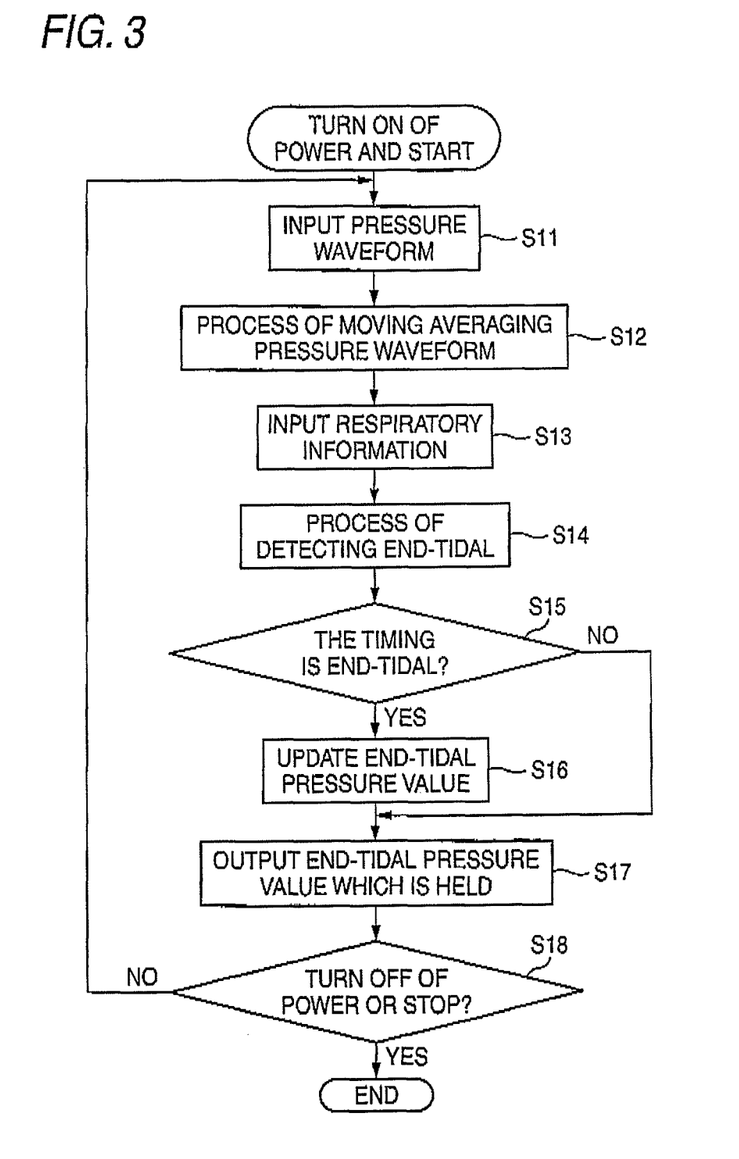
FIG. 3 is a flowchart showing a process of removing variation due to a respiratory component in the embodiment of the biological signal measuring apparatus of the invention.

The analyzing portion 31 of the CPU 30 fetches the pressure waveform signal, and the signal branching portion 35 branches the signal to the end-tidal pressure detecting portion 37. For example, the pressure waveform signal is the CVP. The end-tidal pressure detecting portion 37 receives the signal which is selected by the respiratory waveform signal selecting portion 36, and the CVP serving as the pressure waveform signal which is output from the signal branching portion 35. The end-tidal pressure detecting portion 37 outputs the pressure value which is obtained by the pressure transducer 11 when the end-tidal pressure detecting portion 37 detects the end-tidal based on the respiratory information. The end-tidal pressure detecting portion 37 performs the following operation of the flowchart which is shown in FIG. 3, thereby outputting the pressure value which is obtained by the pressure sensor when the end-tidal is recognized.

When the power supply is turned on and a start button is operated, the operation is started, the CVP waveform which is the blood pressure waveform signal is acquired (S11), and a process for obtaining a moving average is performed (S12). For example, the CVP waveform which is the blood pressure waveform signal is indicated as pWave(i), and the moving average Mean(n) for T seconds is calculated by following Expression 1.

$$\text{Mean}(n) = \frac{1}{k} \sum_{i=n-k}^{n} pWave(i) \quad \text{(Expression 1)}$$

In the above expression, k=T/s, and s indicates the sampling period (for example, 8 ms) with respect to the invasive blood pressure. As T, a preset predetermined time period (for example, 1 second) may be used. Alternatively, one heartbeat period may be obtained from the electrocardiographic waveform signal obtained from the electrocardiogram processing circuit 22, and the one heartbeat period may be set as T. In the case where the one heartbeat period is set as T as described above, the value of T may be updated every predetermined number (one or more) of heartbeat periods. The one heartbeat period may not be obtained from the electrocardiographic waveform signal, but may be obtained from the invasive blood pressure or the artery of a biological signal (a pulse wave or the like) obtained from another sensor.

Figure 4:
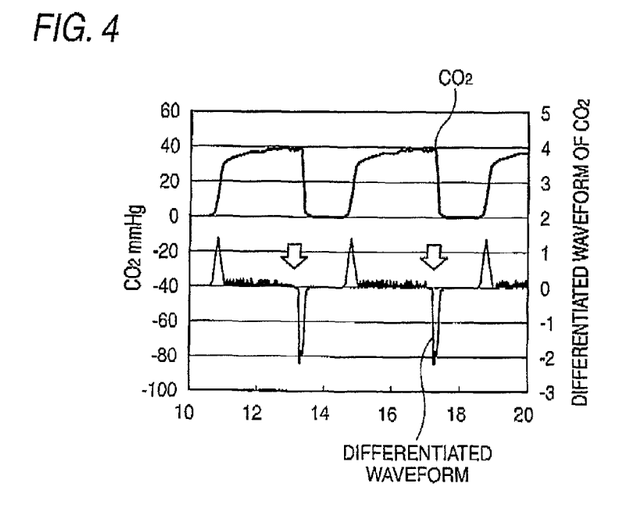
FIG. 4 is a waveform chart illustrating an example of the process of removing variation due to a respiratory component in the embodiment of the biological signal measuring apparatus of the invention.

After step S12, the CPU 30 obtains signal respiratory information of a predetermined sampling period (for example, 8 ms) which is selected by the respiratory waveform signal selecting portion 36 (S13), and detects the end-tidal (S14). The end-tidal is a timing when the expiration is switched to the inspiration. The expiration contains $CO_2$ in the body, and hence the $CO_2$ concentration is high. In the inspiration, the $CO_2$ concentration is substantially equal to that of the atmosphere, and hence has a value near zero. Therefore, the end-tidal is specifically detected in the following manner. The capnograph which is obtained in the mainstream $CO_2$ sensor 13, which is sent from the $CO_2$ concentration processing circuit 24, and which is as shown in FIG. 4 is differentiated to obtain a differentiated waveform. A timing (falling timing) when the differentiated waveform is changed from positive (zero or more) to negative is set to the end-tidal.

In the example, the capnograph which is obtained in the mainstream $CO_2$ sensor 13, and which is sent from the $CO_2$ concentration processing circuit 24 is used. Alternatively, the end-tidal may be detected by detecting the timing when the expiration is switched to the inspiration, from the impedance respiratory waveform signal which is generated by the impedance respiratory processing circuit 23, or the respiratory flow signal or airway pressure Paw signal which is produced by the respiratory flow/airway pressure processing circuit 25.

Specifically, the impedance respiratory waveform signal shows that, in the case of the inspiration, the impedance is high because the air enters the alveoli, and, in the case of the expiration, the impedance is low because the air is discharged from the alveoli. When the changing point of the impedance is detected, therefore, the point can be set as the end-tidal. In the case where the respiratory flow signal is used, the direction of the respiratory flow in the case of the expiration is inverted from that in the case of the inspiration, and therefore the timing of the inversion is detected to be set as the end-tidal. In the case of the airway pressure signal, a peak of an airway pressure signal waveform (airway pressure curve) is detected, and the timing of the peak can be set as the end-tidal.

After the end-tidal detecting process in step S14, it is detected whether the timing is the end-tidal or not (S15), and, if the timing is not the end-tidal, the end-tidal pressure value which is held in the CPU 30 is output (S17). If it is detected in step S15 that the timing is the end-tidal, an updating process in which the CVP at the timing is set as the end-tidal pressure value is performed (S16), and the new end-tidal pressure value is output (S17). In this way, a correct biological signal can be stably output while suppressing respiratory variation included in the biological signal.

Figure 5:
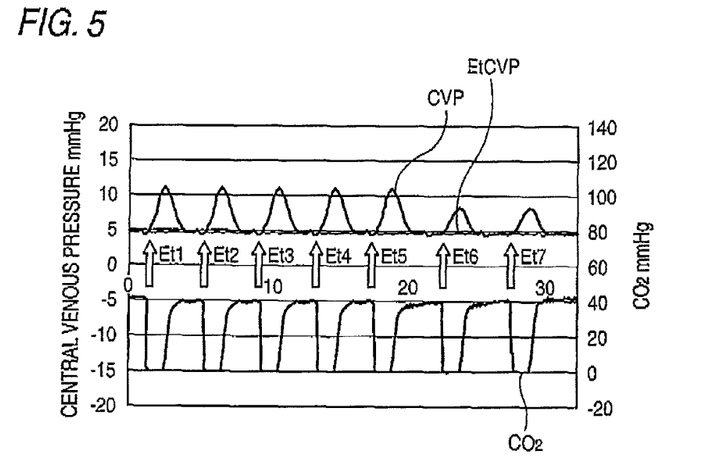
FIG. 5 is a waveform chart illustrating an example of the process of removing variation due to a respiratory component in the embodiment of the biological signal measuring apparatus of the invention.

As a result of the above-described process, end-tidals Et1, Et2, Et3, ... indicated by the arrows which are arranged in a time sequential manner are obtained for the capnograph such as shown in FIG. 5. Then, the values of the CVP at the times which correspond to the end-tidals, respectively are output as the end-tidal pressure value EtCVP. As shown in step S18, in the biological signal measuring apparatus of the embodiment, when the power supply is turned off or a stop button is operated, the process is ended, and, in another case, control is returned to step S11 to continue the process.

Figure 6:
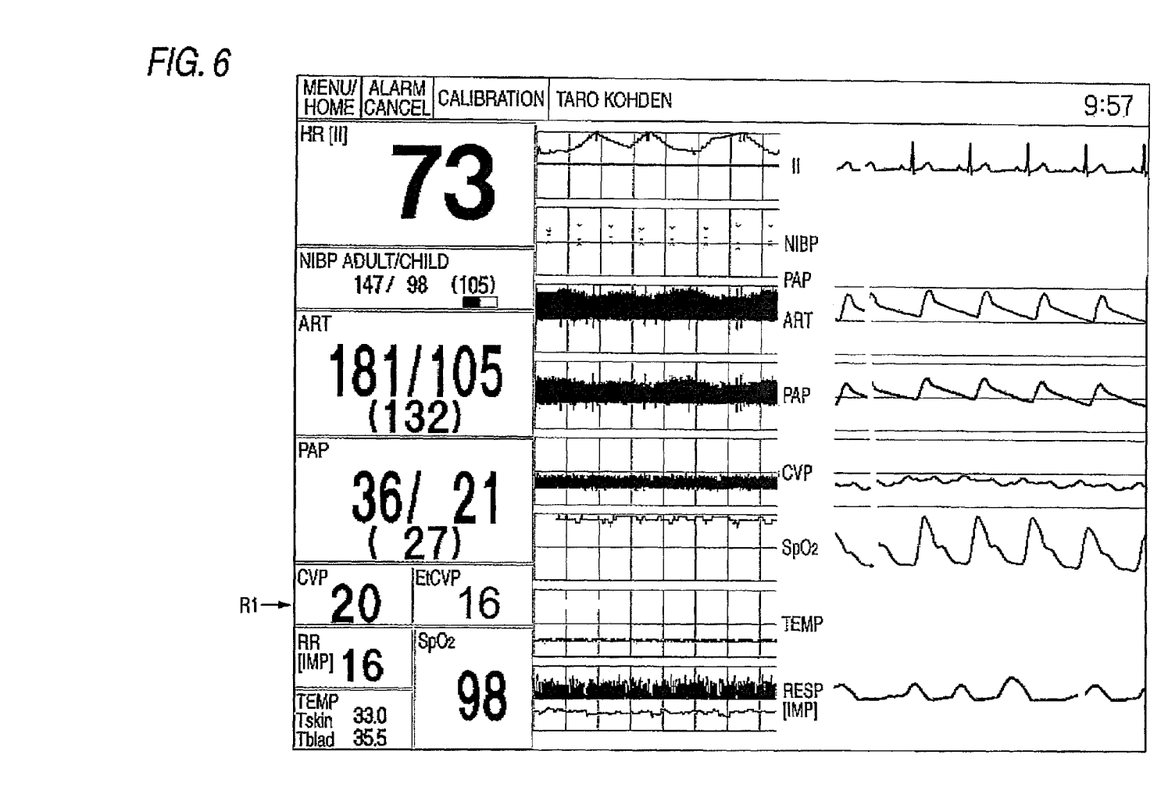
FIG. 6 is a view showing a display example of a biological signal which has been subjected to the process of removing variation due to a respiratory component in the embodiment of the biological signal measuring apparatus of the invention.

FIG. 6 shows a display example of the waveforms/values of respiratory information which are displayed on the waveform/value displaying portion 40 by the above-described output. In the figure, in the row indicated by R1, the moving average value of the CVP which is obtained in step S12 is displayed in the extreme left frame. As illustrated, the end-tidal pressure value (EtCVP) may be independently and simultaneously displayed in the frame right next to that where the moving average value of the CVP is displayed. Alternatively, only a selected one of the values may be displayed. As another value or waveform, the heart rate (HR) and electrocardiogram which are based on the electrocardiographic waveform signal produced by the electrocardiogram processing circuit 22 are displayed. The non-invasive blood pressure (NIBP), the arterial pressure (ART), the intrapleural pressure (PAP), the blood oxygen saturation ($SpO_2$), and the like are obtained by corresponding sensors. These values are displayed the waveform/value displaying portion 40 by the CPU 30.

With respect to the display of the end-tidal pressure value (EtCVP), an inputting device through which an external input to the CPU 30 is to be performed may be disposed, and the setting whether the display is performed or not may be conducted. In place of or together with the central venous pressure (CVP) from the blood pressure sensor for measuring the invasive blood pressure, the pressure transducer 11 may obtain at least one of the pulmonary arterial pressure (RAP), the pulmonary arterial wedge pressure (PCWP), the arterial pressure (ART), and the intracardiac pressure (RAP, RVP, LAP, LVP), and the obtained pressure(s) may undergo the process by the end-tidal pressure detecting portion 37 shown in the flowchart of FIG. 3, so that a correct biological signal can be measured stably while suppressing respiratory variation included in the biological signal.

In the embodiment, the pressure transducer 11 which is a pressure sensor measures the intracranial pressure, and the end-tidal pressure detecting portion 37 which functions as an outputting unit, and which outputs the intracranial pressure value performs the process such as shown in the flowchart of FIG. 3, so that the intracranial pressure which is a correct biological signal can be measured stably while suppressing respiratory variation included in the intracranial pressure serving as a biological signal.

According to an aspect of the invention, a pressure value, which is obtained by the pressure sensor when the end-tidal is detected based on the respiratory information that is obtained by the respiratory sensor, is output. In the configuration, the end-tidal is a timing at which the expiration is ended, and which is immediately before the beginning of the inspiration. At the timing, respiratory variation included in a biological signal such as the invasive blood pressure or the intracranial pressure is suppressed, and a correct biological signal can be stably measured.

According to an aspect of the invention, an actually measured value is output without processing the waveform obtained by the pressure sensor. Therefore, the accuracy of the output result can be maintained at a high level.

According to an aspect of the invention, the respiratory sensor is of the mainstream type. Therefore, a correct end-tidal can be recognized without time delay, respiratory variation included in a biological signal can be adequately suppressed, and a correct biological signal can be stably measured.

According to an aspect of the invention, both of the pressure value output from the outputting unit and the value of the pressure measured by the pressure sensor are simultaneously displayed, or one of them is selectively displayed. When they are largely different from each other, therefore, it is easily known that the pressure measured by the pressure sensor is affected by respiration.

According to an aspect of the invention, the selecting unit selects at least one of the respiratory information which are measured by the plurality of respiratory sensors, respectively. Even in the case where one of the respiratory sensors is disconnected, fails to operate, or detects a large noise, the selecting unit selects the optimum one of the respiratory sensors, so that the excellent pressure measurement can be continued.

What is claimed is:

1. A biological signal measuring apparatus comprising:
   a pressure sensor configured to measure an invasive blood pressure in a living body as a first invasive blood pressure value;
   a respiratory sensor configured to measure respiratory information; and
   an outputting unit configured to detect an end-tidal based on the respiratory information measured by the respiratory sensor and whether said end-tidal has occurred, and
   a displaying portion connected to the outputting unit
   wherein, as a result of detecting the end-tidal, the outputting unit is configured to update the first invasive blood pressure value and to output a second invasive blood pressure, which is an updated value of the first invasive blood pressure value and is based on the invasive blood pressure measured by the pressure sensor when detecting the end-tidal, to be displayed on the displaying portion and
   wherein, as a result of the outputting unit not detecting the end-tidal, a displayed and outputted invasive blood pressure value is held at the first invasive blood pressure value.

2. The biological signal measuring apparatus according to claim 1, wherein
   the pressure sensor is configured to measure at least one of a central venous pressure, a pulmonary arterial pressure, a pulmonary arterial wedge pressure, an arterial pressure, and an intracardiac pressure as the invasive blood pressure.

3. The biological signal measuring apparatus according to claim 1, wherein
   the respiratory sensor is one of an airway pressure sensor, a respiratory flow sensor, a carbon dioxide sensor, a respiratory volume sensor, a respiratory thermal sensor, and an impedance respiratory sensor.

4. The biological signal measuring apparatus according to claim 1, wherein
   the respiratory sensor is of a mainstream type.

5. The biological, signal measuring apparatus according to claim 1, wherein
   the end-tidal is detected from a falling edge of a differentiated waveform of a capnograph.

6. The biological signal measuring apparatus according to claim 1, wherein
   the end-tidal is detected by obtaining a timing when expiration is switched to inspiration in an airway pressure, a respiratory flow, or a respiratory volume waveform.

7. The biological signal measuring apparatus according to claim 1, wherein
   at least one of the first invasive blood pressure value and the second invasive blood pressure value output by the outputting unit corresponds to one of an average pressure obtained by a moving average and an average pressure of one heartbeat period.

8. The biological signal measuring apparatus according to claim 1, wherein at least one of (i) both of a value of the first invasive blood pressure measured by the pressure sensor and the second invasive blood pressure value output by the outputting unit are simultaneously displayed, and (ii) one of the value of the first invasive blood pressure measured by the pressure sensor and the second invasive blood pressure value output by the outputting unit is selectively displayed.

9. The biological signal measuring apparatus according to claim 1, further comprising:
a selecting unit,
wherein
the respiratory sensor includes a plurality of respiratory sensors including an airway pressure sensor, a respiratory flow sensor, a carbon dioxide sensor, a respiratory volume sensor, a respiratory thermal sensor, and an impedance respiratory sensor, and
the selecting unit selects at least one of respiratory information which are measured by the plurality of respiratory sensors.

10. The biological signal measuring apparatus according to claim 1, wherein
the outputting unit updates the first invasive blood pressure, as the second invasive blood pressure value, that is measured by the pressure sensor only at a time point when detecting the end-tidal.

11. The biological signal measuring apparatus according to claim 1, wherein
the outputting unit outputs the second invasive blood pressure that is measured by the pressure sensor in response to the detection of the end-tidal.

12. A biological signal measuring apparatus comprising:
a pressure sensor configured to measure an intracranial pressure in a living body as a first intracranial pressure value;
a respiratory sensor configured to measure respiratory information; and
an outputting unit configured to detect an end-tidal based on the respiratory information measured by the respiratory sensor and whether said end-tidal has occurred, and
a displaying portion connected to the outputting unit
wherein, as a result of detecting the end-tidal, the outputting unit is configured to update the first intracranial pressure value and to output a second intracranial pressure value, which is an updated value of the first intracranial pressure value and is based on the intracranial pressure measured by the pressure sensor when detecting the end-tidal, to be displayed on the displaying portion, and
wherein, as a result of the outputting unit not detecting the end-tidal, a displayed and outputted intracranial pressure value is held at the first intracranial pressure value.

13. The biological signal measuring apparatus according to claim 12, wherein
the respiratory sensor is one of an airway pressure sensor, a respiratory flow sensor, a carbon dioxide sensor, a respiratory volume sensor, a respiratory thermal sensor, and an impedance respiratory sensor.

14. The biological signal measuring apparatus according to claim 12, wherein
the respiratory sensor is of a mainstream type.

15. The biological signal measuring apparatus according to claim 12, wherein,
the end-tidal is detected by from a falling edge of a differentiated waveform of a capnograph.

16. The biological signal measuring apparatus according to claim 12, wherein
the end-tidal is detected by obtaining a timing when expiration is switched to inspiration in an airway pressure, a respiratory flow, or a respiratory volume waveform.

17. The biological signal measuring apparatus according to claim 12, wherein at least one of the intracranial pressure value output and the second intracranial pressure value output
corresponds to one of an average pressure obtained by a moving average and an average pressure of one heartbeat period.

18. The biological signal measuring apparatus according to claim 12,
wherein at least one of (i) both of a value of the first intracranial pressure measured by the pressure sensor and the second intracranial pressure value output by the outputting unit are simultaneously displayed, and (ii) one of the value of the first intracranial pressure measured by the pressure sensor and the second intracranial pressure value output by the outputting unit is selectively displayed.

19. The biological signal measuring apparatus according to claim 12, further comprising:
a selecting unit,
wherein
the respiratory sensor includes a plurality of respiratory sensors including an airway pressure sensor, a respiratory flow sensor, a carbon dioxide sensor, a respiratory volume sensor, a respiratory thermal sensor, and an impedance respiratory sensor, and
the selecting unit selects at least one of respiratory information which are measured by the plurality of respiratory sensors.

* * * * *